(12) United States Patent
Hofer-Kraner

(10) Patent No.: US 10,274,753 B2
(45) Date of Patent: Apr. 30, 2019

(54) SUN PROTECTION DEVICE

(71) Applicant: Optrel Holding AG, Appenzell (CH)

(72) Inventor: Ramon Hofer-Kraner, Herisau (CH)

(73) Assignee: Optrel Holding AG, Appenzell (CH)

( * ) Notice: Subject to any disclaimer, the term of this patent is extended or adjusted under 35 U.S.C. 154(b) by 0 days.

(21) Appl. No.: 15/466,090

(22) Filed: Mar. 22, 2017

(65) Prior Publication Data

US 2017/0276966 A1 Sep. 28, 2017

(30) Foreign Application Priority Data

Mar. 23, 2016 (EP) .................................... 16161958

(51) Int. Cl.
| | |
|---|---|
| *G02C 7/10* | (2006.01) |
| *G02C 7/08* | (2006.01) |
| *G02F 1/133* | (2006.01) |
| *A41D 13/11* | (2006.01) |
| *A61F 9/02* | (2006.01) |

(52) U.S. Cl.
CPC ............. *G02C 7/101* (2013.01); *G02C 7/083* (2013.01); *G02C 7/086* (2013.01); *G02C 7/088* (2013.01); *G02C 7/10* (2013.01); *G02C 7/105* (2013.01); *G02F 1/13318* (2013.01); *A41D 13/1184* (2013.01); *A61F 9/023* (2013.01); *G02C 2202/18* (2013.01); *G02F 2001/13324* (2013.01)

(58) Field of Classification Search
CPC .... G02C 7/101; G02C 7/105; G02C 2202/18; G02C 7/10; G02C 7/088; G02F 1/13318; G02F 2001/13324
USPC ......................................................... 349/13
See application file for complete search history.

(56) References Cited

U.S. PATENT DOCUMENTS

| | | | |
|---|---|---|---|
| 4,873,113 A * | 10/1989 | Grein-Wiegand | ..... B41M 5/281 |
| | | | 349/199 |
| 5,552,841 A | 9/1996 | Gallorini et al. | |
| 6,557,995 B1 * | 5/2003 | Edwards | .................. G02C 7/16 |
| | | | 351/44 |
| 7,970,172 B1 | 6/2011 | Hendrickson | |
| 8,833,937 B2 * | 9/2014 | Shehadeh | .............. G02C 7/101 |
| | | | 351/159.6 |
| 9,395,556 B2 * | 7/2016 | Slater | ...................... G02C 7/021 |
| 9,442,293 B2 * | 9/2016 | Alton | .................. G02B 27/0172 |
| 2009/0073558 A1 * | 3/2009 | Jacobs | .................. G02B 27/017 |
| | | | 359/464 |
| 2009/0204291 A1 | 8/2009 | Cernasov | |

FOREIGN PATENT DOCUMENTS

| | | | |
|---|---|---|---|
| EP | 341519 | * | 11/1989 |
| GB | 2445365 A | | 7/2008 |
| WO | 2014/079574 A1 | | 5/2014 |

OTHER PUBLICATIONS

Search Report dated Sep. 1, 2016 issued in corresponding DE patent application No. 16161958.0 (and partial English translation).

* cited by examiner

*Primary Examiner* — Hoan C Nguyen

(74) *Attorney, Agent, or Firm* — Posz Law Group, PLC

(57) ABSTRACT

The invention is based on a sun protection device, in particular sun spectacles, with at least one optical sun protection filter comprising at least one liquid-crystal cell, with at least one sensor unit configured for capturing a solar irradiation, and with at least one control and/or regulation unit, which is configured for controlling and/or regulating a permeability of the optical sun protection filter depending on a solar irradiation.

Figure 1:
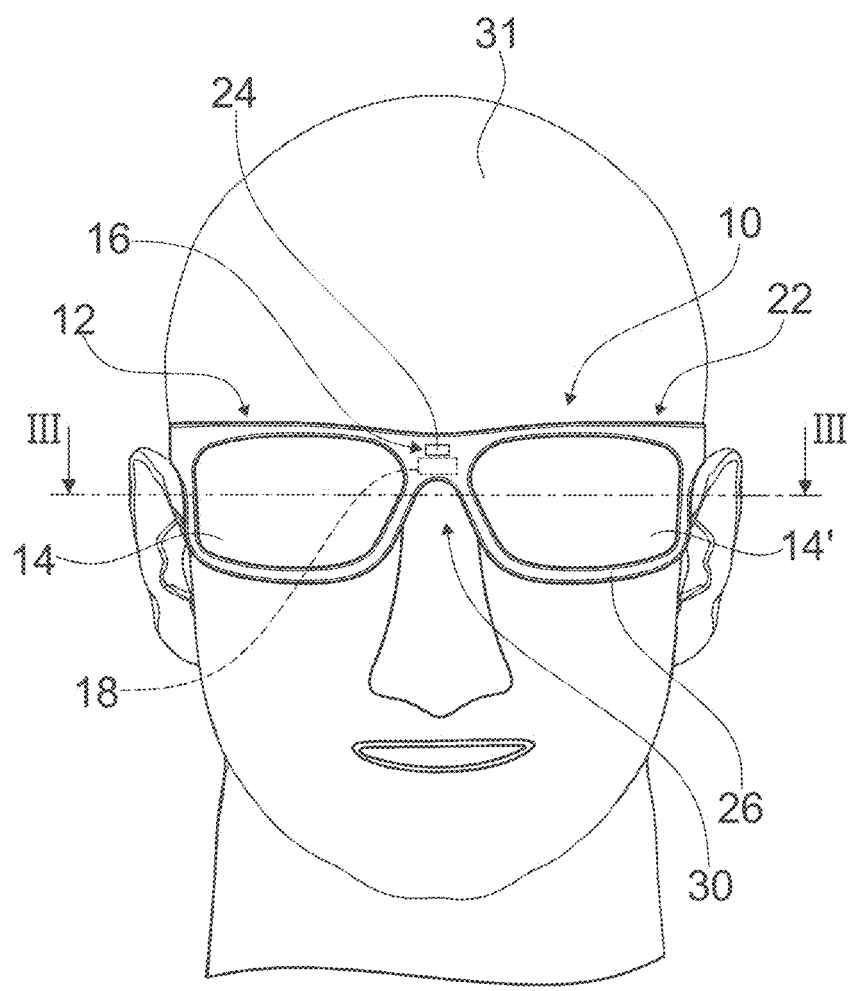

16 Claims, 9 Drawing Sheets

SUN PROTECTION DEVICE

CROSS REFERENCE TO RELATED APPLICATION

This application is based on and incorporates herein by reference European Patent Application No. 16161958.0 filed on Mar. 23, 2016.

STATE OF THE ART

The invention relates to a sun protection device, in particular sun spectacles.

From U.S. Pat. No. 8,081,262 B1 a sun protection device has already been proposed, with at least one optical sun protection filter comprising at least one liquid-crystal cell, with at least one sensor configured for capturing a solar irradiation, and with at least one control and/or regulation unit configured for controlling and/or regulating a permeability of the optical sun protection filter depending on a solar irradiation.

The objective of the invention is in particular to provide a generic device with improved characteristics in regard to comfort as well as to a usability. The objective is achieved, according to the invention, by the features of patent claim 1 while advantageous implementations and further developments of the invention may become apparent from the subclaims.

Advantages of the Invention

The invention is based on a sun protection device, in particular sun spectacles, with at least one optical sun protection filter comprising at least one liquid-crystal cell, with at least one sensor unit configured for capturing a solar irradiation, and with at least one control and/or regulation unit configured for controlling and/or regulating a permeability of the optical sun protection filter depending on a solar irradiation.

It is proposed that the control and/or regulation unit is in at least one operating state configured for controlling the at least one liquid-crystal cell of the optical sun protection filter for generating a permeability gradient, which is defined for a user and features at least two differing permeabilities. Preferentially the control and/or regulation unit is configured, in at least one operating state, for controlling the at least one liquid-crystal cell of the optical sun protection filter for the purpose of generating a permeability gradient with at least two differing permeabilities, which is defined from a viewing direction of the user, in particular the wearer. Preferably the control and/or regulation unit is configured, in at least one operating state, for controlling the at least one liquid-crystal cell of the optical sun protection filter for the purpose of generating a permeability gradient which depends on a viewing angle. Especially preferentially the liquid-crystal cell is in at least one operating state controlled for generating a permeability that depends on a viewing angle and yields, from a user's viewing direction, a defined permeability gradient. Preferably the at least one optical sun protection filter comprises at least two liquid-crystal cells. Preferentially each liquid-crystal cell of the optical sun protection filter is allocated to a user's eye respectively. Principally, however, it would also be conceivable that the at least one optical sun protection filter comprises merely one liquid-crystal cell for both eyes of the user. By a "sun protection device" is, in this context, in particular a device to be understood which is configured for protecting a user's eyes from solar irradiation, in particular bothersome solar irradiation. It is preferably in particular to be understood as a device which is configured for at least reducing a solar irradiation. Particularly preferably the sun protection device is configured, in at least one operating state, for darkening a solar irradiation, in particular a bothersome solar irradiation, on the user's eyes. A variety of implementations of the sun protection device are conceivable which are deemed expedient by someone skilled in the art, e.g. as a sun protection screen and/or especially preferentially as sun spectacles. Furthermore, in this context, an "optical sun protection filter" is in particular to be understood as an optical filter implementing in particular a protective glass and/or a protective synthetic glass, in particular for protection from bothersome solar irradiation. It is preferably in particular to be understood as an optical filter the light permeability of which is implemented adjustable. Preferentially it is in particular to be understood as an optical protection filter with automatic darkening. Especially preferentially the sun protection filter comprises at least one liquid-crystal plane which is switchable in the transmittance. Preferably the optical sun protection filter comprises at least one liquid-crystal cell. A variety of liquid-crystal cells are conceivable which are deemed expedient by someone skilled in the art, e.g. in particular a TN liquid-crystal cell featuring the Twisted Nematic technology. Principally, however, other embodiments of the liquid-crystal cells would also be conceivable which are deemed expedient by someone skilled in the art, e.g. as STN liquid-crystal cells featuring the Super Twisted Nematic technology, DSTN liquid-crystal cells featuring the Double Super Twisted Nematic technology, TSTN liquid-crystal cells featuring the Triple Super Twisted Nematic technology, VA liquid-crystal cells with the Vertical Alignment technology, in particular PVA/MVA liquid-crystal cells with the Patterned Vertical Alignment and/or Multi-Domain Vertical Alignment technology, IPS liquid-crystal cells with the In-Plane Switching technology, FLCD liquid-crystal cells, i.e. ferro-electrical liquid-crystal cells, and/or TN liquid-crystal cells featuring the Guest-Host technology. By a "sensor unit" is, in this context, in particular a unit to be understood which is configured for receiving at least one parameter and/or physical property, wherein the recordal may take place actively, e.g. in particular by generating and emitting an electrical measuring signal, and/or passively, e.g. in particular by capturing property changes of a sensor component. A variety of sensor units for a sun protection device are conceivable which are deemed expedient by someone skilled in the art. Preferably the sensor unit comprises at least one photo cell, in particular a photodiode and/or in particular a solar cell. Preferentially the photo cell is in particular at least configured for an optical detection of sunlight and/or artificial light. Furthermore, in this context, a "control and/or regulation unit" is in particular to be understood as a unit with at least one control electronics component. By a "control electronics component" is in particular a unit to be understood featuring at least one electronic circuit which preferably consists of voltage components and reference control components. Principally the control electronics component may as well have a more complex structure, e.g. in particular using an application-specific integrated circuit (ASIC) and/or a micro-controller component.

In this context, a "permeability of the optical sun protection filter" is in particular to mean a sunlight transmittance intensity through the optical sun protection filter. Preferably it is in particular to mean to which degree the visible spectrum of sunlight is absorbed and/or reflected by the optical sun protection filter. Particularly preferably it is in particular to mean a shade. In this context, a "defined permeability gradient" is furthermore in particular to mean a local progression of a permeability of the liquid-crystal cell which is visible to a user, in particular a wearer. It is preferably to mean, in particular, a progression of a permeability of the liquid-crystal cell which is visible from the user's, in particular the wearer's, viewing direction and which features at least two differing permeabilities at a fix point in time. Preferentially it is in particular to mean a local progression of a permeability of the liquid-crystal cell which is visible to a user, in particular a wearer, and which is generated by the optical properties of the liquid crystals of the liquid-crystal cell itself. The defined permeability gradient herein in particular results from the angle-dependency of the liquid-crystal cell, i.e. an influence on the transmittance of the liquid-crystal cell depending on a viewing angle of the user's eye onto the crystal molecules and depending on the orientation of the crystal molecules. With increasing angling of the viewing direction, respectively the viewing angle, with respect to the crystal molecules of the liquid-crystal cell, in particular the transmittance of the liquid-crystal cell decreases and absorption is increased. Furthermore, in this context, the term "differing permeabilities" is in particular to mean that the at least one liquid-crystal cell comprises, at least from the view of the user, in particular the wearer, at least two regions which have, from a viewing direction, respectively a viewing angle, of the user, in particular the wearer, shades which are substantially different from each other. Herein the term "substantially different shades" is in particular to mean a difference between the shades of at least 1%, preferably at least 10% and particularly preferably at least 30%. A shade herein in particular defines a percental light absorption at least in the range of visible light, in particular in a wavelength range of 380 nm to 780 nm. "Configured" is in particular to mean specifically programmed, designed and/or equipped. By an object being configured for a certain function is in particular to be understood that the object fulfils and/or implements said certain function in at least one application state and/or operating state.

By the sun protection device according to the invention, in particular a darkening is achievable which is advantageously comfortable for a user. In particular, by the permeability gradient of the liquid-crystal cell occurring from the user's viewing direction, a darkening may be provided to the user which is adapted to a solar irradiation. In particular a high level of comfort as well as an advantageous usability of the sun protection device may be provided.

It is further proposed that the control and/or regulation unit is in at least one operating state configured for controlling the at least one liquid-crystal cell of the optical sun protection filter for the purpose of maintaining the permeability gradient defined for the user. Preferably the control and/or regulation unit is configured for controlling, in case of constant solar irradiation with respect to the sun protection device, the at least one liquid-crystal cell of the optical sun protection filter for the purpose of maintaining the permeability gradient that is defined from the user's viewing direction. The term "maintaining the defined permeability gradient" is, in this context, in particular to mean maintaining the permeability gradient, which is present at a point in time and is defined from the user's viewing direction, over an infinite period. It is preferably in particular to mean maintaining the permeability gradient defined from the user's viewing direction which is present at a point in time over a period in which a solar irradiation remains at least substantially constant with respect to the sun protection device. Particularly preferably it is in particular to mean maintaining an alignment of the crystal molecules of the liquid-crystal cell, which alignment is present at a fix point in time, and with which alignment the permeability gradient is generated that is defined from a user's viewing direction, over a period in which a solar irradiation remains at least substantially constant with respect to the sun protection device. In this way, a permeability gradient may be reliably maintained in the liquid-crystal cell permanently. In particular, in this way a progression that is visible from the user's viewing direction may be generated permanently. It is in this way achievable that a user is provided with maximum vision at optimum darkening.

It is also proposed that for a user a lower permeability of the at least one liquid-crystal cell is arranged below a higher permeability in the permeability gradient. Preferably the permeability gradient extends, from a viewing direction of a user, from top to bottom, wherein a permeability increases from top to bottom. A darkening decreases in the permeability gradient from top to bottom, in particular from a viewing direction of a user. Herein "below" is in particular to mean below in a regular position of the sun protection device. It is preferably in particular to mean below in a state when the sun protection device is worn by a user, in case of an upright posture of the user. It is thus in particular to mean below from the user's view. In this way in particular a darkening is achievable which is advantageously comfortable for a user. Preferentially, as a result of this an upper side of the liquid-crystal cell, which faces towards the sun and on which the sun rays radiate onto the at least one liquid-crystal cell, can be darkened to a higher degree, in particular in case of an upright posture of the operator. This allows achieving that a user is provided with maximum sight at optimum darkening.

Furthermore it is proposed that the control and/or regulation unit is in at least one operating state configured for adjusting an intensity and/or extension of the permeability gradient of the at least one liquid-crystal cell of the optical sun protection filter for a user, depending on a solar irradiation. Preferably the control and/or regulation unit is in at least one operating state configured for adjusting an extension of the permeability gradient of the at least one liquid-crystal cell of the optical sun protection filter from a viewing direction of a user depending on a solar irradiation, wherein thus an average permeability over the area of the at least one liquid-crystal cell is changed for a user. Preferentially the control and/or regulation unit is configured for adjusting a permeability gradient of the at least one liquid-crystal cell of the optical sun protection filter, which permeability gradient is defined and determined from a viewing direction of a user, wherein a position of the permeability gradient is changed depending on a solar irradiation. With increasing solar irradiation, from a user's viewing direction in particular an average permeability decreases over the area of the at least one liquid-crystal cell. Preferably, from the user's viewing direction, the permeability gradient extends with increasing solar irradiation farther and farther into the liquid-crystal cell, in particular from top to bottom. In this way in particular a darkening is achievable that is advantageously comfortable and adapted for a user. It is furthermore achievable that at optimum darkening a user is provided with maximum vision.

Alternatively or additionally it would also be conceivable that the control and/or regulation unit is in at least one operating state configured for adjusting an intensity and/or extension of the permeability gradient of the at least one liquid-crystal cell of the optical sun protection filter for a user, depending on at least one user input. Preferably the control and/or regulation unit is in at least one operating state configured for adjusting an intensity and/or extension of the permeability gradient of the at least one liquid-crystal cell of the optical sun protection filter for a user, depending on a user-adjustable level for adapting the permeability gradient. Preferably a user input and/or an input of the user-adjustable level is effected via an input unit. Particularly preferably the user input herein in particular defines a corrective factor, a multiplicative factor and/or an extreme value, in particular a minimum value and/or particularly preferably a maximum value of the permeability gradient defined for a user, in particular with respect to the solar irradiation. Principally it would, however, also be conceivable that the permeability gradient that is defined for a user can be fixed to a defined value by a user via the user input. By an "input unit" is, in this context, in particular a unit to be understood via which adjustments can be made, in particular by a user. Preferentially it is in particular to be understood as a unit which is configured for receiving an input value from a user in an adjustment process. Preferably the unit is configured to be contacted, in particular directly contacted, by an operator, wherein touching the input unit and/or an actuation force applied onto an operating element of the input unit and/or a position of the input unit changed by a user are/is sensed. Principally, however, merely a current position of the input unit may be captured. In this way the permeability gradient defined for a user is individually adaptable and/or adjustable in particular by a user.

It is moreover proposed that the control and/or regulation unit is in at least one operating state configured for controlling and/or regulating a control voltage, for the purpose of controlling the at least one liquid-crystal cell of the optical sun protection filter, to a value below a saturation field strength of the at least one liquid-crystal cell. Preferably the control and/or regulation unit is in at least one operating state configured for controlling and/or regulating a control voltage for the purpose of controlling the at least one liquid-crystal cell of the optical sun protection filter to a value below a saturation voltage required for supplying a saturation field strength of the at least one liquid-crystal cell of the optical sun protection filter. Preferentially the control and/or regulation unit is configured for controlling and/or regulating a control voltage for the purpose of controlling the at least one liquid-crystal cell of the optical sun protection filter to a value below the saturation voltage. Especially preferably the difference between a bright region and a dark region of the liquid-crystal cell increases with increasing control voltage. As long as the control voltage is operated below the saturation voltage required for supplying a saturation field strength of the at least one liquid-crystal cell, the difference between the bright region and dark region of the liquid-crystal cell in particular remains constant. As soon as the control voltage reaches the saturation voltage required for supplying a saturation field strength of the at least one liquid-crystal cell, the user would in particular perceive a lighting-up in an upper region. By a "control voltage" is, in this context, in particular a voltage to be understood which is applied to electrodes, in particular electrode layers, of the at least one liquid-crystal cell for the purpose of generating an electrical field for aligning a liquid-crystal layer of the at least one liquid-crystal cell. Furthermore, in this context, a "saturation field strength" is in particular to mean a minimum limit field strength required for an at least approximately complete alignment, in particular structured arrangement, of the liquid-crystal layer of the at least one liquid-crystal cell. It is preferably in particular to mean a minimum limit field strength required to induce a dipole moment necessary for a complete alignment of the liquid-crystal layer of the at least one liquid-crystal cell. This advantageously allows providing a permeability gradient of the at least one liquid-crystal cell of the optical sun protection filter in a structurally simple fashion. Furthermore in this way, in particular at optimum darkening, an advantageously low energy consumption of the sun protection device is achievable.

It is also proposed that the at least one liquid-crystal cell of the optical sun protection filter is embodied at least partly curved. Preferably the at least one liquid-crystal cell of the optical sun protection filter is embodied in such a way that it is curved over a substantial extension. Preferentially the at least one liquid-crystal cell of the optical sun protection filter is embodied substantially curved. By "at least partly in a curved fashion" is, in this context, in particular to be understood that the liquid-crystal cell features, viewed in at least one plane, a curvature differing from zero. Herein a "curvature" differing from zero in a point of an area is, in this context, in particular to mean a deviation from a tangential plane increasing, at a power of two, with a distance to the point of the area. "Substantially curved" is, in this context, in particular to mean that a maximum distance of the liquid-crystal cell from a tangential plane is, in a center of the liquid-crystal cell, at least 2 mm, preferably at least 4 mm and especially preferentially at least 6 mm when viewed perpendicularly to the tangential plane. In this way in particular an advantageously high optical quality of the sun protection device may be rendered available. In particular, an advantageously low angle difference is achievable between the optical paths of the respective eyes. In particular an irritating see-through view, especially in a peripheral region of the sun protection device, is avoidable. Moreover a high ergonomy level of the sun protection device is achievable. It is in particular avoidable that the user's eyelashes touch the at least one liquid-crystal cell.

Furthermore it is proposed that the at least one liquid-crystal cell of the optical sun protection filter is implemented by a synthetic liquid-crystal cell. Preferably the liquid-crystal cell is at least partly made of synthetics, in particular of polycarbonate. Especially preferentially at least one limiting disk of the liquid-crystal cell is made of synthetics, in particular of polycarbonate. It would, however, principally also conceivable that the at least one liquid-crystal cell of the optical sun protection filter is embodied by a glass liquid-crystal cell. Herein it would be in particular conceivable that the at least one liquid-crystal cell is manufactured at least partly of curved glass. In this way a weight of the sun protection device may advantageously be kept low. Moreover, by using synthetic liquid-crystal cells an advantageously high-degree of UV protection may be provided, in particular due to absorption in the synthetics material, in particular in the polycarbonate.

It is further proposed that the sun protection device comprises a spectacle frame which is configured for accommodating the optical sun protection filter. Preferably the spectacle frame comprises two accommodating regions, each of which is respectively configured for accommodating a liquid-crystal cell of the at least one optical sun protection filter. By a "spectacle frame" is, in this context, in particular a frame to be understood which is configured for arranging the sun protection device on a user's face. Preferably the frame is configured for arranging the sun protection device on a user's nose and ears. Especially preferentially the spectacle frame is embodied by a spectacle framing. This in particular allows achieving an advantageous implementation of the sun protection device. Preferably the sun protection device may thus be reliably arranged in a user's face. In particular a spectacles-like implementation of the sun protection device can be provided.

It is also proposed that the at least one sensor unit is in at least one operating state configured for at least partly supplying an energy for controlling the at least one liquid-crystal cell of the optical sun protection filter. Preferably the at least one sensor unit is in at least one operating state configured for fully supplying an energy for controlling the at least one liquid-crystal cell of the optical sun protection filter. Preferentially the at least one sensor unit is, during operation of the sun protection device, configured for fully supplying an energy for controlling the at least one liquid-crystal cell of the optical sun protection filter. Especially preferentially the at least one sensor unit is during operation of the sun protection device configured for full production of an energy required for controlling the at least one liquid-crystal cell of the optical sun protection filter. Preferably the sun protection device is embodied battery-free. This in particular allows dispensing with an external energy supply, e.g. via a battery and/or via an accumulator. A self-sustaining sun protection device may be made available.

It is further proposed that the at least one sensor unit comprises at least one photodiode. Preferably the sensor unit comprises at least one solar cell. Preferentially the sensor unit is implemented by a solar cell and/or a photocell. In this way an advantageously reliable sensor unit with an advantageously high energy yield may be provided. Moreover, in particular an external energy supply, e.g. via a battery and/or via an accumulator, may be dispensed with. When a photocell is used, in particular a sensor unit may be rendered available via which in particular light in a non-visible range, e.g. in particular infrared light, may be captured and preferably used as well. A self-sustaining sun protection device may be rendered available. This in particular allows achieving that with increasing solar irradiation more energy is available for controlling the at least one liquid-crystal cell of the optical sun protection filter. An energy production is thus advantageously adapted to an energy demand.

The invention is furthermore based on a method for operating the sun protection device. It is proposed that the at least one liquid-crystal cell of the optical sun protection filter is controlled and/or regulated for generating a permeability gradient defined for a user. Preferably the at least one liquid-crystal cell of the optical sun protection filter is controlled for generating a permeability gradient featuring at least two differing permeabilities which is defined from a user's viewing direction. In this way in particular a darkening is achievable which is advantageously comfortable for a user. In particular, by the permeability gradient occurring from a user's viewing direction, the user can be provided with a darkening that is adapted to a solar irradiation. In this way it is achievable that at optimum darkening, a user is provided with maximum sight. In particular, a high level of comfort as well as advantageous usability of the sun protection device may be rendered available.

Furthermore it is proposed that the at least one liquid-crystal cell of the optical sun protection filter is controlled and/or regulated depending on a solar irradiation for generating a permeability gradient defined for a user. Preferably the at least one liquid-crystal cell of the optical sun protection filter is controlled and/or regulated depending on a solar irradiation for generating a permeability gradient defined from a user's viewing direction. In this way in particular a darkening is achievable which is advantageously comfortable for a user. In particular, in this way a permeability gradient can be adapted to an actual solar irradiation. In particular an individual adaption of the permeability gradient to a solar irradiation is achievable.

It is moreover proposed that the at least one liquid-crystal cell of the optical sun protection filter is controlled and/or regulated, depending on at least one user input, for generating a permeability gradient defined for a user. Preferably a user input is effected via an input unit. Particularly preferably the user input herein defines in particular a corrective factor, a multiplicative factor and/or an extreme value, in particular a minimum value and/or especially preferentially a maximum value, of the permeability gradient that is defined for a user, in particular with respect to the solar irradiation. Principally it would however also be conceivable that the permeability gradient that is defined for a user can be fixed to a defined value by a user via the user input. In this way the permeability gradient defined for a user is in particular individually adaptable and/or adjustable by a user. This allows achieving that a user is supplied with maximum vision at optimum darkening. A high level of comfort as well as advantageous usability of the sun protection device can be made available.

Furthermore it is proposed that the at least one liquid-crystal cell of the optical sun protection filter is controlled and/or regulated, depending on a user-adjustable level for adapting the permeability gradient, for the purpose of generating a permeability gradient defined for a user. Preferably the level is selectable via an input unit. Especially preferentially the user-adjustable level herein in particular defines a corrective factor and/or a multiplicative factor of the permeability gradient defined for a user, in particular with respect to the solar irradiation. In this way the permeability gradient defined for a user is in particular individually adaptable and/or adjustable by a user. This allows achieving that with optimum darkening a user is supplied with maximum sight. A high level of comfort as well as advantageous usability of the sun protection device may in particular be made available.

The sun protection device according to the invention as well as the method are herein not to be restricted to the application and implementation described above. In particular the sun protection device according to the invention and the method may, for fulfilling a functionality herein described, a number of respective elements, structural components and unit which differs from a number herein mentioned.

DRAWINGS

Further advantages will become apparent from the following description of the drawings. In the drawings an exemplary embodiment of the invention is shown. The drawings, the description and the claims contain a plurality of features in combination. Someone skilled in the art will purposefully also consider the features separately and will find further expedient combinations.

Figure 2:
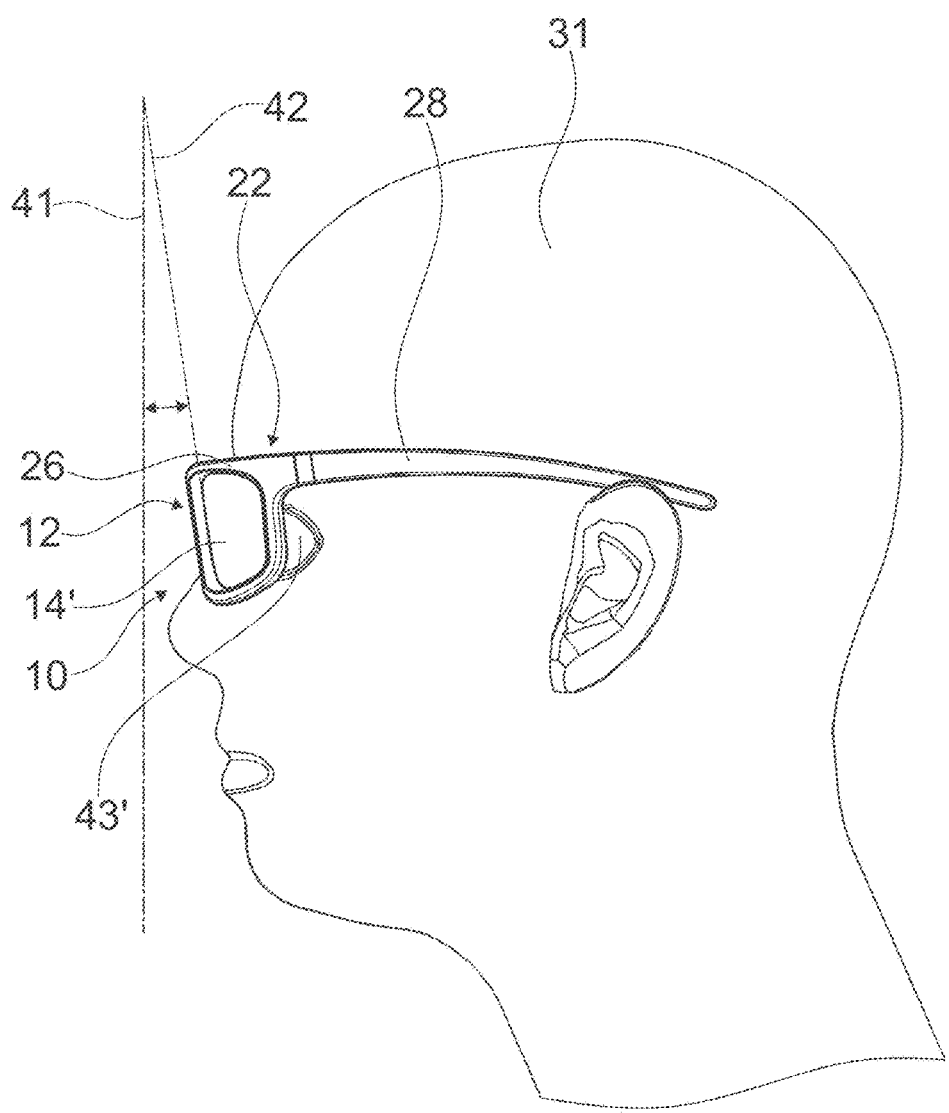
Figure 3:
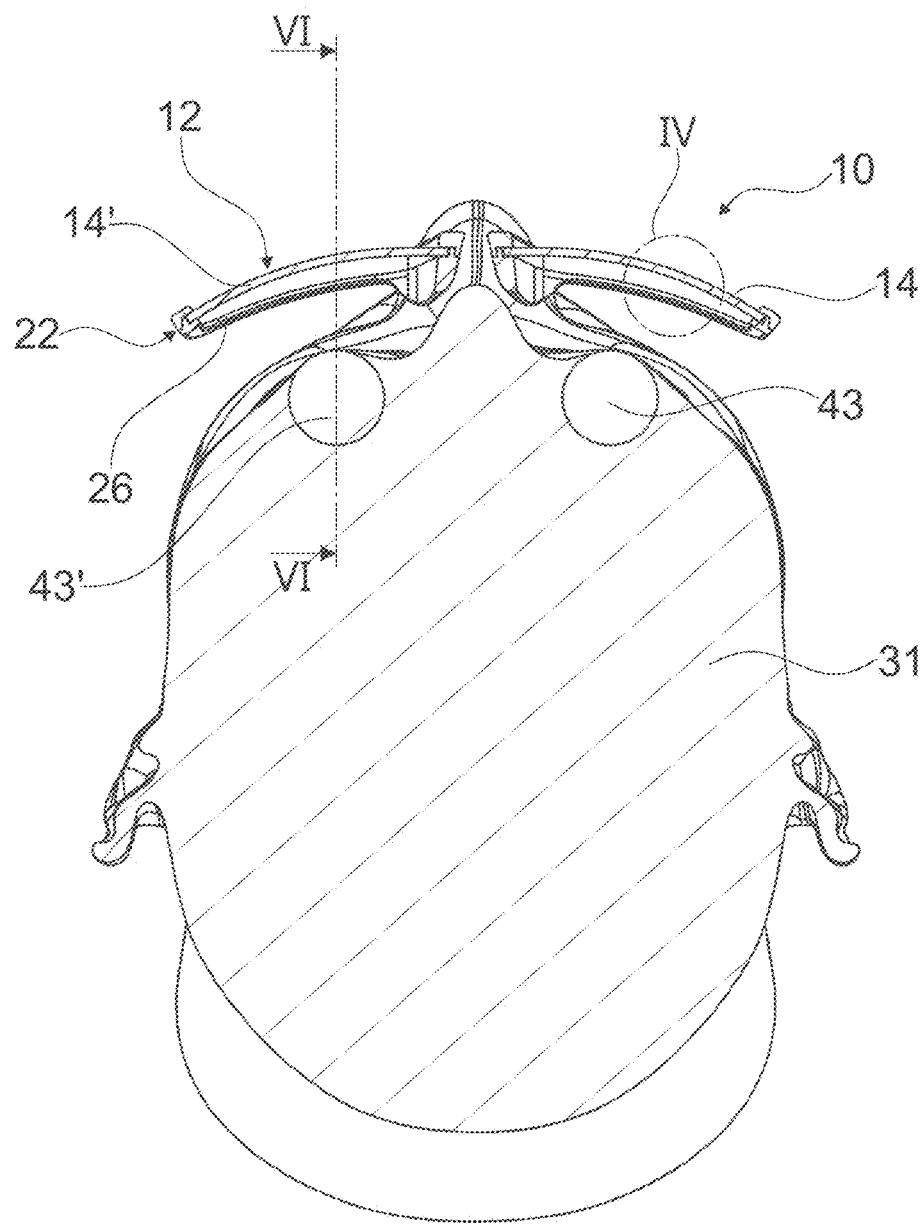
Figure 4:
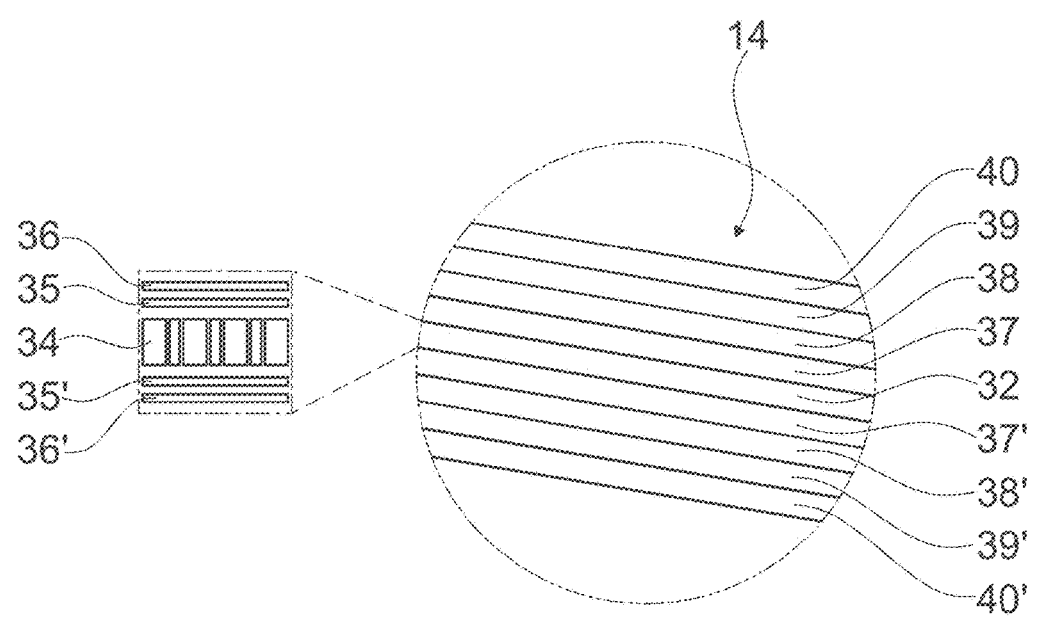
Figure 5:
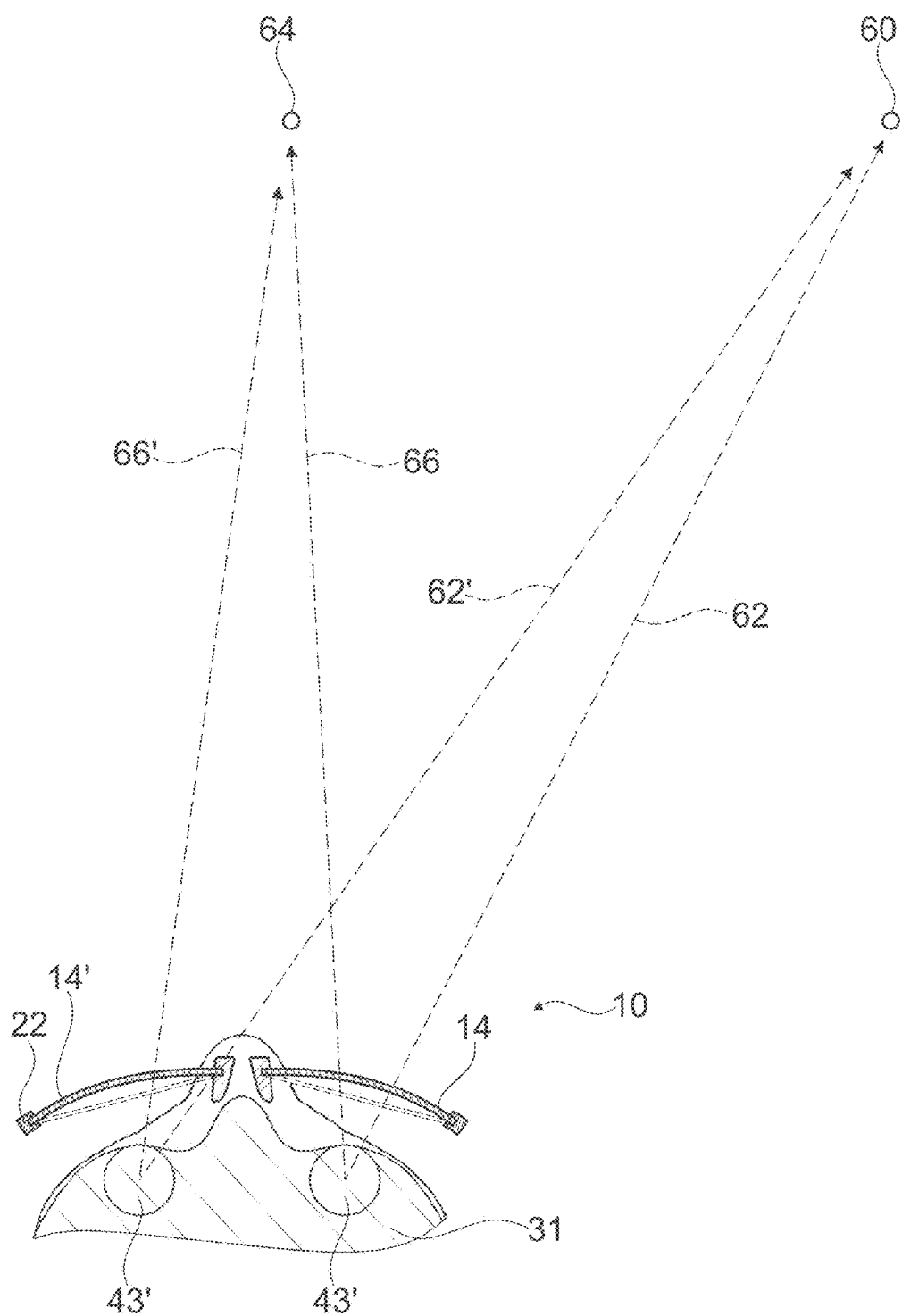
Figure 6:
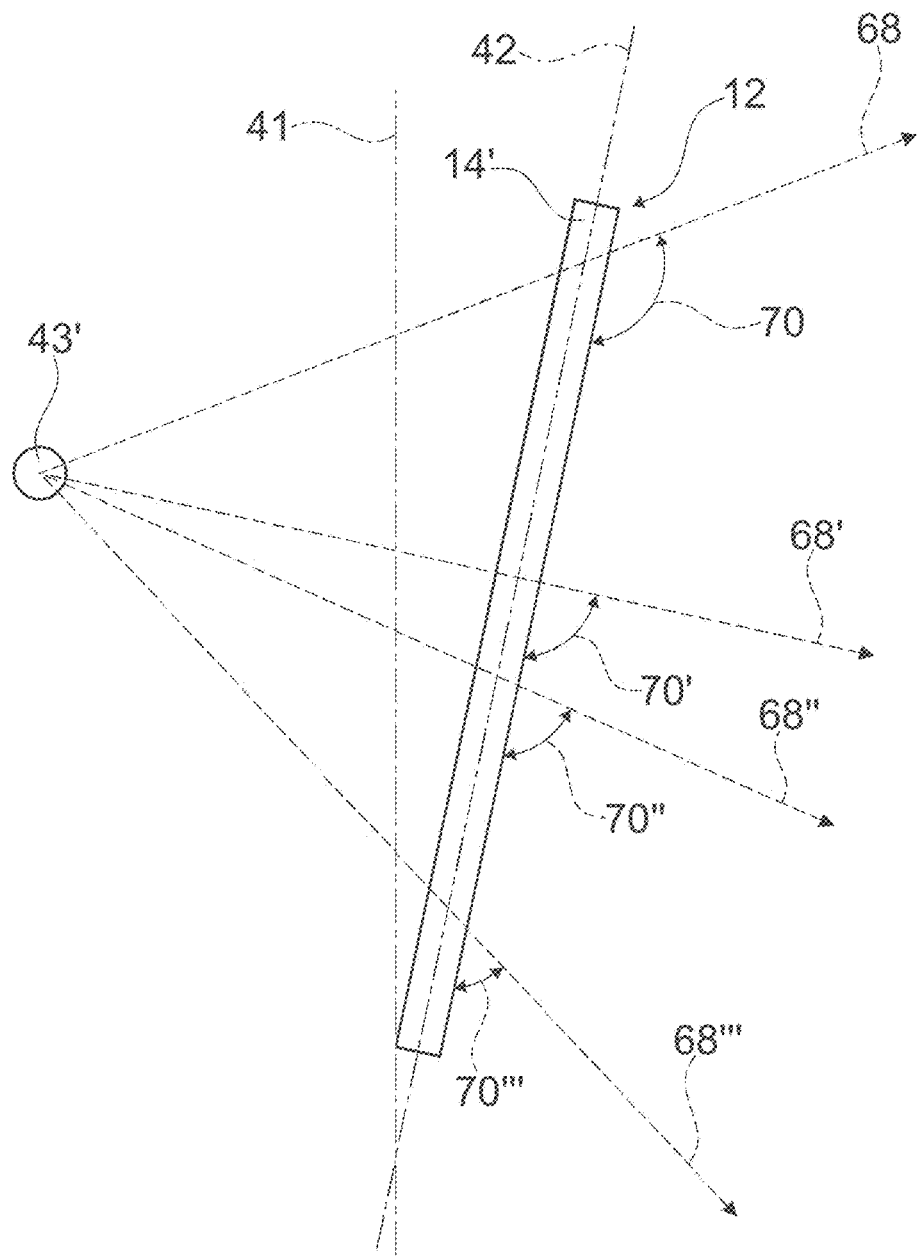
Figure 7:
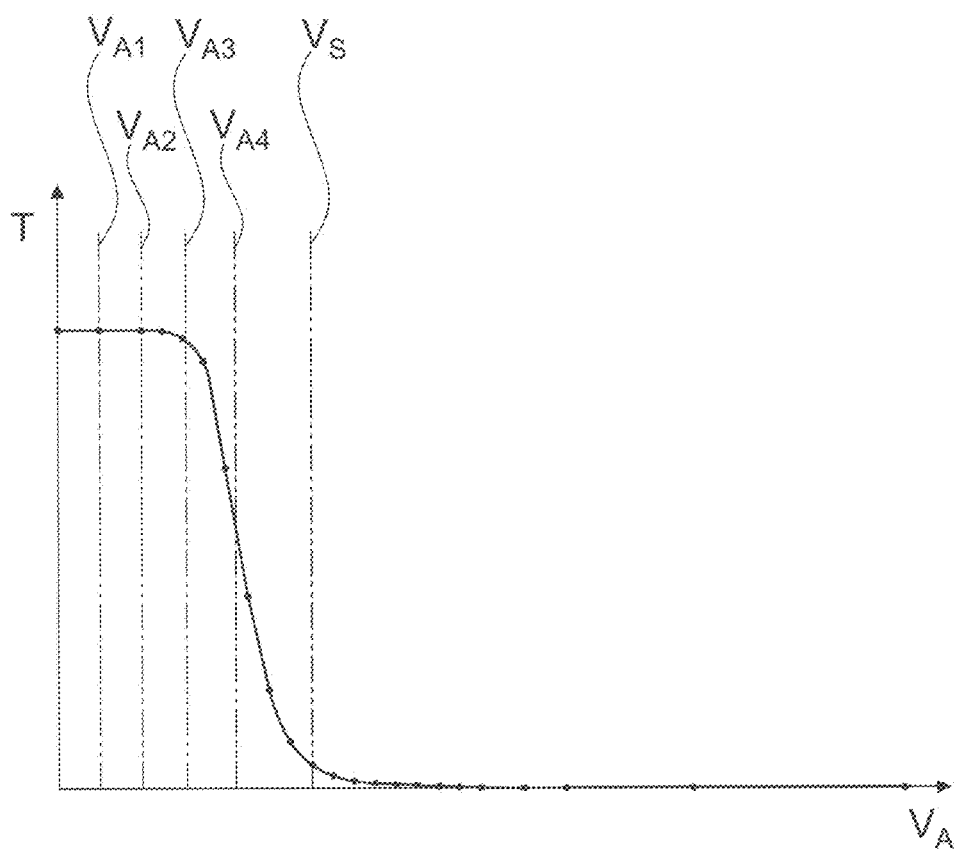
Figure 8A:
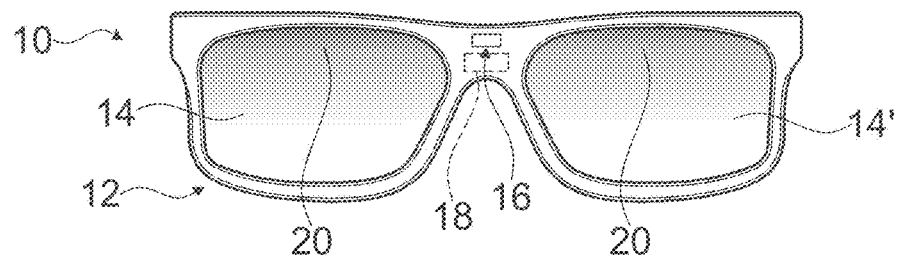
Figure 8B:
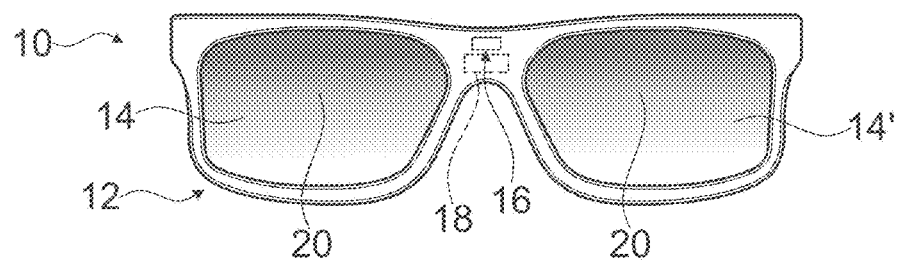
Figure 8C:
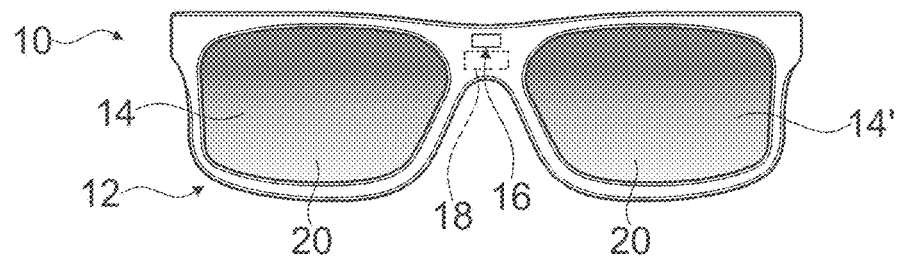
Figure 8D:
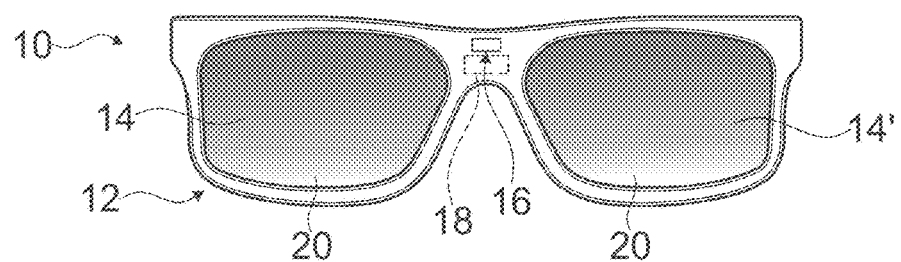
Figure 9:
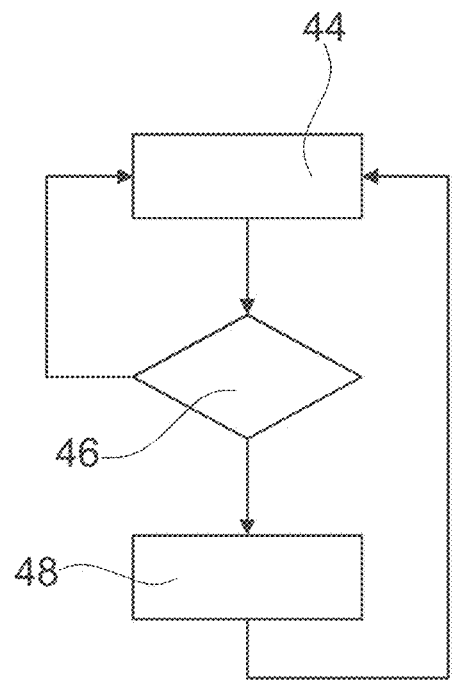
Figure 10:
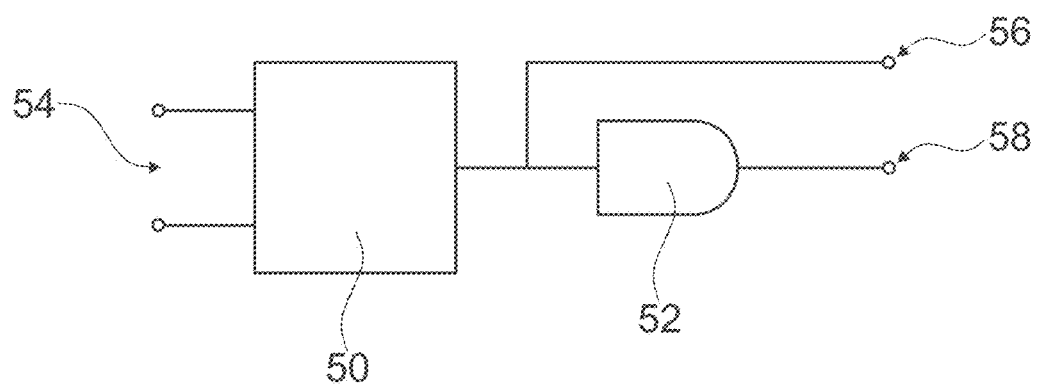

It is shown in:

FIG. 1 a sun protection device according to the invention with a sun protection filter comprising two liquid-crystal cells, with a sensor unit and with a control and regulation unit, as well as a user wearing the sun protection device according to the invention, in a schematic front view, FIG. 2 the sun protection device according to the invention and the user wearing the sun protection device according to the invention, in a schematic lateral view, FIG. 3 the sun protection device according to the invention and the user wearing the sun protection device according to the invention, in a schematic sectional view along the section line III, FIG. 4 a partial section IV-IV of the sun protection device according to the invention with the sun protection filter, in a schematic sectional view, FIG. 5 the sun protection device according to the invention and the user, in a schematic sectional view along the section line III with different viewing angles of the user, FIG. 6 the sun protection device according to the invention and the user, in a schematic sectional view along the section line VI with different viewing angles of the user, FIG. 7 a diagram of a transmittance of the liquid-crystal cells of the sun protection filter, depending on a control voltage, FIG. 8A a permeability gradient of the liquid-crystal cells of the sun protection device according to the invention, in a first state, FIG. 8B a permeability gradient of the liquid-crystal cells of the sun protection device according to the invention, in a second state, FIG. 8C a permeability gradient of the liquid-crystal cells of the sun protection device according to the invention, in a third state, FIG. 8D a permeability gradient of the liquid-crystal cells of the sun protection device according to the invention, in a fourth state, FIG. 9 a flow chart of a method for operating the sun protection device according to the invention, and FIG. 10 a schematic switch diagram of the control and regulation unit of the sun protection device according to the invention.

DESCRIPTION OF THE EXEMPLARY EMBODIMENT

FIGS. 1 and 2 show a sun protection device 10. The sun protection device 10 is implemented by a pair of sun spectacles. The sun protection device 10 is implemented by sun spectacles darkening automatically depending on a solar irradiation. Principally, however, another implementation of the sun protection device 10 would also be conceivable which is deemed expedient by someone skilled in the art. The sun protection device 10 comprises a spectacle frame 22. The spectacle frame 22 is embodied by a spectacle framing. The spectacle frame 22 is substantially made of synthetics. Principally, however, another material would also be conceivable which is deemed expedient by someone skilled in the art. The spectacle frame 22 comprises a base frame 26 as well as two spectacle earpieces 28, which are movably supported on the base frame 26 and only one of which is visible. The base frame 26 comprises a nose cut-out 30 to be supported on a nose of a user 31. The spectacle earpieces 28 are each configured to be supported on the ears of the user 31.

The sun protection device 10 furthermore comprises an optical sun protection filter 12. The spectacle frame 22 is configured for accommodating the optical sun protection filter 12. The optical sun protection filter 12 is accommodated in the spectacle frame 22. A light permeability of the optical sun protection filter 12 is implemented adjustable. The optical sun protection filter 12 is embodied substantially transparent, wherein a transmittance T of the optical sun protection filter 12 is implemented electrically modifiable. The optical sun protection filter 12 comprises two liquid-crystal cells 14, 14'. The liquid-crystal cells 14, 14' are embodied mirror-symmetrically with respect to each other. The liquid-crystal cells 14, 14' are accommodated in the spectacle frame 22. The base frame 26 of the spectacle frame 22 features two recesses, in which the liquid-crystal cells 14, 14' are accommodated. The liquid-crystal cells 14, 14' are respectively arranged on sides of the nose cut-out 30 which are situated opposite each other. Each of the liquid-crystal cells 14, 14' of the optical sun protection filter 12 is allocated to respectively one eye of the user 31. The liquid-crystal cells 14, 14' each comprise a liquid-crystal plane 32 which is switchable in the transmittance T.

The liquid-crystal cells 14, 14' of the optical sun protection filter 12 are each embodied by a synthetics liquid-crystal cell. The liquid-crystal cells 14, 14' respectively consist of a plurality of layers. A number of layers is herein merely given as an example and may principally vary. The liquid-crystal cells 14, 14' are each implemented by a TN liquid-crystal cell. The liquid-crystal cells 14, 14' are hence based on the Twisted-Nematic technology. Principally, however, other implementations of the liquid-crystal cells 14, 14' would also be conceivable which are deemed expedient by someone skilled in the art, e.g. as STN liquid-crystal cells with the Super-Twisted-Nematic technology, DSTN liquid-crystal cells with the Double-Super-Twisted-Nematic technology, TSTN liquid-crystal cells with the Triple-Super-Twisted-Nematic technologogy, VA liquid-crystal cells with the Vertical-Alignment technology, in particular PVA/MVA liquid-crystal cells with the Patterned-Vertical-Alignment or Multi-Domain-Vertical-Alignment technology, IPS liquid-crystal cells with the In-Plane-Switching technology, FLCD liquid-crystal cells, i.e. ferro-electrical liquid-crystal cells, and/or TN liquid-crystal cells with the Guest-Host technology. The liquid-crystal cells 14, 14' each feature a liquid-crystal plane 32. The liquid-crystal plane 32 is embodied by a translucent liquid-crystal plane. The liquid-crystal plane 32 features a liquid-crystal layer 34. In the liquid-crystal layer 34 there are a plurality of crystal molecules as well as spacers. On both sides of the liquid-crystal layer 34 a polyimide layer 35, 35' is respectively arranged. The polyimide layers 35, 35' in particular serve for aligning the crystal molecules. On the sides of the polyimide layers 35, 35' which face away from the liquid crystal layer 34, an electrode layer 36, 36' is respectively arranged. The electrode layers 36, 36' are respectively implemented by a transparent indium-tin-oxide layer. There is furthermore a polarization layer 37, 37' respectively arranged on both sides of the liquid-crystal plane 32 of the liquid-crystal cells 14, 14'. The polarization layers 37, 37' respectively serve for a polarization of incident light. On the sides of the polarization layers 37, 37' which face away from the liquid-crystal plane 32, a disk 38, 38' is respectively arranged. The disks 38, 38' are made of synthetics. The disks 38, 38' are made of polycarbonate. On an outer side of the disks 38, 38' an anti-reflection layer 39, 39' and a hard coating 40, 40' have been respectively applied. The liquid-crystal cells 14, 14' of the optical sun protection filter 12 are respectively embodied at least partly curved. The liquid-crystal cells 14, 14' of the optical sun protection filter 12 are each embodied curved over an entire extension (FIG. 4).

FIG. 5 shows the sun protection device 10 and the user 31 with different viewing angles of the user 31, viewed in a horizontal plane. A first viewing angle of the user 31 onto a first point 60 is shown. The first point 60 is situated in a peripheral region of the field of vision of the user 31. A viewing direction 62 of the first eye 43 of the user 31 onto the first point 60 extends through the curved liquid-crystal cell 14 at an angle of 83 degrees. A viewing direction 62' of the second eye 43' of the user 31 onto the first point 60 extends through the curved liquid-crystal cell 14' at an angle of 126 degrees. A difference between the two viewing directions 62, 62' of the two eyes 43, 43' of the user 31 is therefore 43 degrees. In the same arrangement the difference would be in case of planar liquid-crystal cells approximately 63 degrees. Furthermore, a second viewing angle of the user 31 onto a second point 64 is shown. The second point 64 is situated in a center of the field of vision of the user 31. A viewing direction 66 of the first eye 43 of the user 31 onto the second point 64 extends through the curved liquid crystal cell 14 at an angle of 103 degrees. A viewing direction 66' of the second eye 43' of the user 31 onto the second point 64 extends through the liquid-crystal cell 14' at an angel of 107 degrees. A difference between the two viewing directions 66, 66' of the two eyes 43, 43' of the user 31 is therefore 4 degrees. In the same arrangement the difference would be in case of planar liquid-crystal cells approximately also 4 degrees. The curved implementation of the liquid-crystal cells 14, 14' therefore allows generating an advantageously constant image in particular in peripheral regions of the field of vision of the user 31 as well. In particular, disturbing differences between the two eyes 43, 43' of the user 31 are achievable.

The sun protection device 10 further comprises a sensor unit 16. The sensor unit 16 is configured for capturing a solar irradiation. The sensor unit 16 is arranged in the spectacle frame 22. The sensor unit 16 is arranged in the base frame 26 of the spectacle frame 22 between the recesses for the liquid-crystal cells 14, 14'. The sensor unit 16 is arranged in the base frame 26 of the spectacle frame 22 above the nose cut-out 30. The sensor unit 16 is uncovered towards a front side of the sun protection device 10. The sensor unit 16 comprises a photodiode 24. The sensor unit 16 comprises a photocell. Principally it would, however, also be conceivable that the sensor unit 16 comprises a solar cell. The sensor unit 16 comprises a photodiode embodied by a photocell. The sensor unit 16 is implemented by the photodiode 24.

The sun protection device 10 further comprises a control and regulation unit 18. The control and regulation unit 18 is configured for controlling a permeability of the optical sun protection filter 12 depending on a solar irradiation. The control and regulation unit 18 is for this purpose connected to the sensor unit 16 in a manner that is not visible in detail. Moreover the control and regulation unit 18 is connected to the liquid-crystal cells 14, 14' of the optical sun protection filter 12 in a manner that is not visible in detail. The control and regulation unit 18 is electrically connected to the electrode layers 36, 36' of the liquid-crystal cells 14, 14' in a manner that is not visible in detail. The control and regulation unit 18 is arranged in the spectacle frame 22. The control and regulation unit 18 is arranged in the base frame 26 of the spectacle frame 22 between the recesses for the liquid-crystal cells 14, 14'. The control and regulation unit 18 is arranged in the base frame 26 of the spectacle frame 22 above the nose cut-out 30. Principally, however, a different arrangement of the control and regulation unit 18, which is deemed expedient by someone skilled in the art, would also be conceivable. The control and regulation unit 18 is constantly in operation and is in particular not de-activatable. The control and regulation unit 18 switches on from a defined voltage applied at the sensor unit 16 and starts oscillating. Principally it would however also be conceivable that the control and regulation unit 18 could be set into operation by means of switch that is not visible in detail.

The control and regulation unit 18 is in one operating state configured for controlling the liquid-crystal cells 14, 14' of the optical sun protection filter 12 for generating a permeability gradient 20 that is defined for a user 31, with at least two differing permeabilities. The control and regulation unit 18 is in case of a solar irradiation configured for controlling the liquid-crystal cells 14, 14' of the optical sun protection filter 12 for generating a permeability gradient 20 that is defined from a viewing direction of the user 31, with at least two differing permeabilities. The control and regulation unit 18 is in case of a solar irradiation configured for controlling the liquid-crystal cells 14, 14' of the optical sun protection filter 12 for generating a continuous permeability gradient 20 that is defined from a viewing direction of the user 31, with at least two differing permeabilites. In the permeability gradient 20 a lower permeability of the liquid-crystal cells 14, 14' of the optical sun protection filter 12 is for a user 31 arranged below a higher permeability. The permeability gradient 20 therefore extends for a user 31 from top to bottom, wherein a permeability increases from top to bottom. The permeability gradient 20 furthermore extends, from a viewing direction of the user 31, in parallel to a main extension plane 42 of the respective liquid-crystal cell 14, 14'. The main extension plane 42 of the liquid-crystal cells 14, 14' features, in case of an upright posture of the user 31, an angle of 12 degrees with respect to a vertical 41. The control and regulation unit 18 is in one operating state configured for controlling the liquid-crystal cells 14, 14' of the optical sun protection filter 12 for maintaining the permeability gradient 20 which is defined for a user 31. The control and regulation unit 18 is configured, in case of constant solar irradiation with respect to the sun protection device 10, for controlling the liquid-crystal cells 14, 14' of the optical sun protection filter 12 for maintaining the permeability gradient 20 that is defined from a viewing direction of the user 31. Furthermore, the control and regulation unit 18 is in one operating state configured for adjusting an intensity as well as an extension of the permeability gradient 20 of the liquid-crystal cells 14, 14' of the optical sun protection filter 12 for a user 31 depending on a solar irradiation. The control and regulation unit 18 is herein configured for adjusting an extension of the permeability gradient 20 of the liquid-crystal cells 14, 14' of the optical sun protection filter 12 from a viewing direction of the user 31, depending on a solar irradiation, thus changing an average permeability over the area of the liquid-crystal cells 14, 14'. With increasing solar irradiation herein an average permeability changes over an area of the liquid-crystal cells 14, 14', from a viewing direction of the user 31. In addition, the control and regulation unit 18 is configured for adjusting an extension of the permeability gradient 20 of the liquid-crystal cells 14, 14' of the optical sun protection filter 12 for the user 31 depending on a user input. The control and regulation unit 18 is configured for adjusting an intensity and extension of the permeability gradient 20 of the liquid-crystal cells 14, 14' of the optical sun protection filter 12 for the user 31 depending on a user-adjustable level for adapting the permeability gradient 20. An input of the user-adjustable level is effected via an input unit, which is not shown in detail. The user-adjustable level herein defines a corrective factor of the permeability gradient 20 defined for the user 31 with respect to the solar irradiation. The permeability gradient 20 extends, from a viewing direction of the user 31, with increasing solar irradiation farther and farther from top to bottom into the liquid-crystal cells 14, 14'. The permeability gradient 20 is herein visible for a user 31 in a state when the sun protection device 10 is worn, and is generated by the optical properties of the liquid crystals of the liquid-crystal cells 14, 14' themselves. The defined permeability gradient 20 is herein created by the angle-dependency of the liquid-crystal cells 14, 14', i.e. an influence on the transmittance of the liquid-crystal cells 14, 14', depending on a viewing angle of the eyes 43, 43' of the user 31 onto the crystal molecules of the liquid-crystal layer 34 and depending on an orientation of the crystal molecules. With increasing angling of the viewing direction, respectively the viewing angle, with respect to the crystal molecules of the liquid-crystal layer 34 of the liquid-crystal cell 14, 14', the transmittance of the liquid-crystal cell 14, 14' decreases and absorption is increased.

FIG. 6 shows the sun protection device 10 and the user 31 with different viewing angles of the user 31 through the liquid-crystal cell 14', viewed in a vertical plane. A first viewing angle of the user 31 with a first viewing direction 68 is shown. The first viewing direction 68 extends through the liquid-crystal cell 14' in an upper region of the liquid-crystal cell 14'. The first viewing direction 68 extends through the liquid-crystal cell 14' with a first look-through angle 70. The first look-through angle 70 is approximately 123 degrees. Furthermore a second viewing angle of the user 31 with a second viewing direction 68' is shown. The second viewing direction 68' extends through the liquid-crystal cell 14' below the first viewing direction 68 in a middle region of the liquid-crystal cell 14'. The second viewing direction 68' extends through the liquid-crystal cell 14' with a second look-through angle 70'. The second look-through angle 70' is approximately 90 degrees. Furthermore a third viewing angle of the user 31 with a third viewing direction 68" is shown. The third viewing direction 68" extends through the liquid-crystal cell 14' below the second viewing direction 68' in a middle region of the liquid-crystal cell 14'. The third viewing direction 68" extends through the liquid-crystal cell 14' with a third look-through angle 70". The third look-through angle 70" is approximately 77 degrees. Moreover a fourth viewing angle of the user 31 with a fourth viewing direction 68''' is shown. The fourth viewing direction 68''' extends through the liquid-crystal cell 14' below the third viewing direction 68" in a lower region of the liquid-crystal cell 14'. The fourth viewing direction extends through the liquid-crystal cell 14' with a fourth look-through angle 70'''. The fourth look-through angle 70''' is approximately 55 degrees. With increasing lowering of a vision thus a look-through angle of the user 31 through the liquid-crystal cell 14' is also lowered. Due to the viewing-angle dependency of the liquid-crystal cells 14, 14', thus the transmittance of the liquid-crystal cell increases, at least during operation, with decreasing angling of the viewing direction, respectively the viewing angle, with respect to the crystal molecules of the liquid-crystal layer 34 of the liquid-crystal layer 34 of the liquid-crystal cells 14, 14', and an absorption is reduced. A transmittance of the fourth viewing direction 68''' of the user 31 is therefore, during operation of the sun protection device 10, substantially greater than a transmittance of the first viewing direction 68 of the user 31. A defined permeability gradient 20 for the user 31 is generated.

The control and regulation unit 18 is in one operating state configured to control a control voltage $V_A$ for controlling the liquid-crystal cells 14, 14' of the optical sun protection filter 12 to a value below a saturation field strength of the liquid-crystal cells 14, 14'. For generating the permeability gradient 20, the control and regulation unit 18 is configured to control a control voltage $V_A$ for controlling the liquid-crystal cells 14, 14' of the optical sun protection filter 12 to a value below a saturation voltage $V_S$ required for supplying a saturation field strength of the liquid-crystal cells 14, 14'. The saturation voltage $V_S$ for supplying a saturation field strength of the liquid-crystal cells 14, 14' constitutes a saturation voltage. The liquid-crystal cells 14, 14' of the optical sun protection filter 12 are principally controlled via a control voltage $V_A$, which is smaller than the saturation voltage $V_S$. With increasing solar irradiation the control voltage $V_A$ is raised. The control voltage $V_A$ is herein the voltage applied to the electrode layers 36, 36' of the liquid-crystal cells 14, 14' to generate an electrical field for an alignment of the liquid-crystal layer 34 of the liquid-crystal cells 14, 14'. When a control voltage $V_A$, which is below a saturation voltage $V_S$ required for supplying a saturation field strength of the liquid-crystal cells 14, 14', is applied, the crystal molecules of the liquid-crystal layer 34 of the liquid-crystal cells 14, 14' are only partly deflected, as a result of which there is a viewing-angle dependency of the liquid-crystal cells 14, 14'. For the user 31 the permeability gradient 20 is generated in the liquid-crystal cells 14, 14'.

FIG. 7 shows a diagram of a transmittance T of the liquid-crystal cells 14, 14' of the sun protection filter 12 in dependency of a control voltage $V_A$. Herein the transmittance T is entered on a vertical y-axis, while the control voltage $V_A$ is entered on the horizontal x-axis. The diagram herein shows the average transmittance T of the liquid-crystal cells 14, 14' over the area in percent, depending on a control voltage $V_A$. The diagram also shows the saturation voltage Vs. In case of control voltages $V_A$ which are greater than zero and smaller than the saturation voltage $V_S$, there is a permeability gradient 20 from a viewing direction of the user.

In FIGS. 8A, 8B, 8C and 8D four different states of the sun protection device 10 are respectively shown as examples. FIGS. 8A, 8B, 8C and 8D herein respectively show the permeability gradient 20 of the liquid-crystal cells 14, 14' of the optical sun protection filter 12 in the respective states, wherein in the diagram of FIG. 4 the respective control voltage $V_A$ is shown, which is in the respective state applied to the electrode layers 36, 36' of the liquid-crystal cells 14, 14'. The control voltage $V_{A1}$ is herein allocated to the first state, which is shown in FIG. 8A. The control voltage $V_{A2}$ is herein allocated to the second state, which is shown in FIG. 8B. The control voltage $V_{A3}$ is herein allocated to the third state, which is shown in FIG. 8C. The control voltage $V_{A4}$ is herein allocated to the fourth state, which is shown in FIG. 8D. In the first state there is a solar irradiation which is low with respect to the other states. In the fourth state there is a solar irradiation which is high with respect to the other states. The control voltage $V_A$ is increased with increasing solar irradiation.

The sensor unit 16 is in one operating state configured for at least partly supplying an energy for controlling the liquid-crystal cells 14, 14' of the optical sun protection filter 12. The sensor unit 16 is during operation of the sun protection device 10 configured for completely supplying an energy for controlling the liquid-crystal cells 14, 14' of the optical sun protection filter 12. The sensor unit 16 is during operation of the sun protection device 10 configured for completely producing an energy required for controlling the liquid-crystal cell 14, 14' of the optical sun protection filter 12. The sensor unit 16 supplies the control voltage $V_A$. Moreover, because of this the sun protection device 10 is embodied battery-free.

FIG. 9 shows a flow chart of a method for operating a sun protection device 10. In the method liquid-crystal cells 14, 14' of the optical sun protection filter 12 are controlled for generating a permeability gradient 20 defined for the user. For generating a permeability gradient 20 defined for the user, the liquid-crystal cells 14, 14' of the optical sun protection filter 12 are controlled depending on a solar irradiation. By means of the sensor unit 16 a solar irradiation is captured in a step 44. Then a value of the voltage generated by the sensor unit 16 is monitored in a branching 46. If a threshold value is not exceeded, step 44 is repeated. If the value of the voltage generated by the sensor unit 16 exceeds a certain value, in a further step 48 an oscillation is generated at the level of the sensor voltage via an astable multivibrator 50, thus allowing the AC voltages for controlling the liquid-crystal cells 14, 14' to be generated by way of a subsequently switched NAND gate 52. In addition, the liquid-crystal cells 14, 14' of the optical sun protection filter 12 are controlled for generating the permeability gradient 20 that is defined for the user, depending on a user input. The liquid-crystal cells 14, 14' of the optical sun protection filter 12 are controlled for generating the permeability gradient 20 that is defined for the user, depending on a user-adjustable level for adapting the permeability gradient.

FIG. 10 shows a schematic switch diagram of the control and regulation unit 18. On an input side 54 of the control and regulation unit 18 the sensor unit 16 is arranged. On both output sides 56, 58 of the control and regulation unit 18 the electrode layers 36, 36' of the liquid-crystal cells 14, 14' are arranged.

The invention claimed is:

1. A sun protection device, in particular sun spectacles, comprising:
   at least one optical sun protection filter, the at least one optical sun protection filter further comprising at least one liquid-crystal cell;
   at least one sensor unit configured for capturing a solar irradiation; and
   at least one control and/or regulation unit, which is configured for controlling and/or regulating a permeability of the at least one optical sun protection filter depending on the solar irradiation,
   wherein the at least one control and/or regulation unit is in at least one operating state configured for controlling the at least one liquid-crystal cell of the at least one optical sun protection filter for generating a permeability gradient, which is defined for a user and features at least two differing permeabilities in each of the at least one liquid-crystal cell,
   wherein the at least one liquid-crystal cell is in at least one operating state controlled for generating a permeability that depends on a viewing angle and yields, from a user's viewing direction, a defined permeability gradient,
   wherein the defined permeability gradient results from the angle-dependency of the at least one liquid-crystal cell,
   wherein with increasing solar irradiation, from a user's viewing direction an average permeability decreases over the area of the at least one liquid-crystal cell,
   wherein the at least one control and/or regulation unit is in at least one operating state configured to control a control voltage for controlling the at least one liquid-crystal cell of the at least one optical sun protection filter to a value below a saturation field strength of the at least one liquid-crystal cell,
   wherein the at least one sensor unit is during operation of the sun protection device configured for full production of an energy required for controlling the at least one liquid-crystal cell of the at least one optical sun protection filter, and
   wherein the sensor unit is configured to capture infrared light.

2. The sun protection device according to claim 1,
   wherein the control and/or regulation unit is in at least one operating state configured for controlling the at least one liquid-crystal cell of the optical sun protection filter for maintaining the permeability gradient which is defined for the user over a period in which the solar irradiation remains at least substantially constant with respect to the sun protection device.

3. The sun protection device according to claim 1,
   wherein for a user a region of lower permeability of the at least one liquid-crystal cell is arranged below a region of higher permeability in the permeability gradient, and
   wherein the difference between the permeabilities results in a difference between shades of the regions of at least 1%.

4. The sun protection device according to claim 1,
   wherein the control and/or regulation unit is in at least one operating state configured for adjusting, depending on a solar irradiation, an intensity and/or extension of the permeability gradient of the at least one liquid-crystal cell of the optical sun protection filter for the user.

5. The sun protection device according to claim 1,
   wherein the control and/or regulation unit is in at least one operating state configured for controlling and/or regulating a control voltage, for controlling the at least one liquid-crystal cell of the optical sun protection filter, to values below a saturation field strength of the at least one liquid-crystal cell, and
   wherein the values of the control voltage are allocated to different shading states, in which the crystal molecules of the liquid-crystal layer of the liquid-crystal cells are only partly deflected.

6. The sun protection device according to claim 1,
   wherein the at least one liquid-crystal cell of the optical sun protection filter is embodied at least partly curved.

7. The sun protection device according to claim 1,
   wherein the at least one liquid-crystal cell of the optical sun protection filter comprises at least one limiting disk, wherein the at least one limiting disk is made of synthetics.

8. The sun protection device according to claim 1,
   further comprising a spectacle frame configured for accommodating the optical sun protection filter.

9. The sun protection device according to claim 8,
   wherein the spectacle frame is substantially made of synthetics.

10. The sun protection device according to claim 1,
    wherein the at least one sensor unit is in at least one operating state configured for at least partly supplying an energy for controlling the at least one liquid-crystal cell of the optical sun protection filter.

11. The sun protection device according to claim 1,
    wherein the at least one sensor unit comprises at least one photodiode.

12. The sun protection device according to claim 1,
    wherein the at least one sensor unit comprises at least one solar cell.

13. A method for operating a sun protection device, in particular sun spectacles, the sun protection device comprising:
    at least one optical sun protection filter, the at least one optical sun protection filter further comprising at least one liquid-crystal cell;
    at least one sensor unit configured for capturing a solar irradiation; and at least one control and/or regulation unit, which is configured for controlling and/or regulating a permeability of the at least one optical sun protection filter depending on the solar irradiation, the method comprising:

controlling, by the at least one control and/or regulation unit, in at least one operating state, the at least one liquid-crystal cell of the at least one optical sun protection filter to generate a permeability gradient, which is defined for a user and features at least two differing permeabilities in the at least one liquid-crystal cell;

generating, by the at least one liquid-crystal cell, in at least one operating state, a permeability that depends on a viewing angle and yields, from a user's viewing direction, a defined permeability gradient, wherein the defined permeability gradient results from the angle-dependency of the at least one liquid-crystal cell, and wherein with increasing solar irradiation, from a user's viewing direction, an average permeability decreases over the area of the at least one liquid-crystal cell; and controlling, by the at least one control and/or regulation unit, in at least one operating state, a control voltage for controlling the at least one liquid-crystal cell of the at least one optical sun protection filter to a value below a saturation field strength of the at least one liquid-crystal cell, wherein the at least one sensor unit is, during operation of the at least one sun protection device, configured for full production of an energy required for controlling the at least one liquid-crystal cell of the at least one optical sun protection filter, wherein the at least one sensor unit is configured to capture infrared light, and wherein the at least one liquid-crystal cell of the at least one optical sun protection filter is controlled and/or regulated for generating a permeability gradient defined for a user.

14. The method according to claim 13, wherein the at least one liquid-crystal cell of the optical sun protection filter is controlled and/or regulated depending on a solar irradiation for generating a permeability gradient defined for a user.

15. The method according to claim 13, wherein the at least one liquid-crystal cell of the optical sun protection filter is controlled and/or regulated, depending on at least one user input, for generating a permeability gradient that depends on a viewing angle and yields, from a user's viewing direction, a defined permeability gradient for a user.

16. The method according to claim 15, wherein the at least one liquid-crystal cell of the optical sun protection filter is controlled and/or regulated, depending on a user-adjustable level for adapting the permeability gradient, for generating a permeability gradient defined for a user.

\* \* \* \* \*